United States Patent [19]
Oikawa

[11] Patent Number: 5,625,661
[45] Date of Patent: Apr. 29, 1997

[54] X-RAY CT APPARATUS

[75] Inventor: Shirou Oikawa, Shiga, Japan

[73] Assignee: Shimadzu Corporation, Kyoto, Japan

[21] Appl. No.: 695,523

[22] Filed: Aug. 12, 1996

Related U.S. Application Data

[63] Continuation of Ser. No. 429,299, Apr. 24, 1995, abandoned.

[30]  Foreign Application Priority Data

Apr. 30, 1994 [JP] Japan .................................. 6-114765

[51] Int. Cl.$^6$ .................................................. G01N 23/00
[52] U.S. Cl. .................... 378/15; 378/4; 378/19
[58] Field of Search .................... 378/4, 19, 15

[56]  References Cited

U.S. PATENT DOCUMENTS

| | | | |
|---|---|---|---|
| 4,002,917 | 1/1977 | Mayo | 378/19 |
| 4,250,425 | 2/1981 | Gabbay | 378/137 |
| 4,541,107 | 9/1985 | Rossi et al. | 378/146 |

FOREIGN PATENT DOCUMENTS

| | | | |
|---|---|---|---|
| 1528574 | 10/1978 | United Kingdom | 378/19 |

*Primary Examiner*—Craig E. Church
*Attorney, Agent, or Firm*—Nikaido, Marmelstein, Murray & Oram LLP

[57]  ABSTRACT

An X-ray CT apparatus includes an X-ray generator revolvable to describe a circular path on a plane of revolution, and having a plurality of X-ray focal spots (focal positions) arranged in a direction perpendicular to the plane of revolution; an X-ray detector opposed to the X-ray generator, and having a plurality of detecting elements arranged in a direction along a circumferential edge of the plane of revolution and in the direction perpendicular to the plane of revolution; a revolution controller for revolving the X-ray generator and the X-ray detector without varying a positional relationship therebetween, and outputting angle information; a moving device for moving the object introduced into a space between the X-ray generator and the X-ray detector, relative to the X-ray generator and the X-ray detector, during a revolution of the X-ray generator, in the direction perpendicular to the plane of revolution, by a distance exceeding a width of at least one of the detecting elements per revolution of the X-ray generator, the moving device outputting moving amount information indicative of the distance; an X-ray focal position controller for successively switching the plurality of focal positions of the X-ray generator in response to the revolution by the revolution controller, and outputting focal position information; and an image reconstruct unit operable in response to data from the X-ray detector, the angle information from the revolution controller, the moving amount information from the moving device, and the focal position information from the X-ray focal position controller, for reconstructing a three-dimensional image relating to the object by reversely projecting the data in helical form.

9 Claims, 13 Drawing Sheets

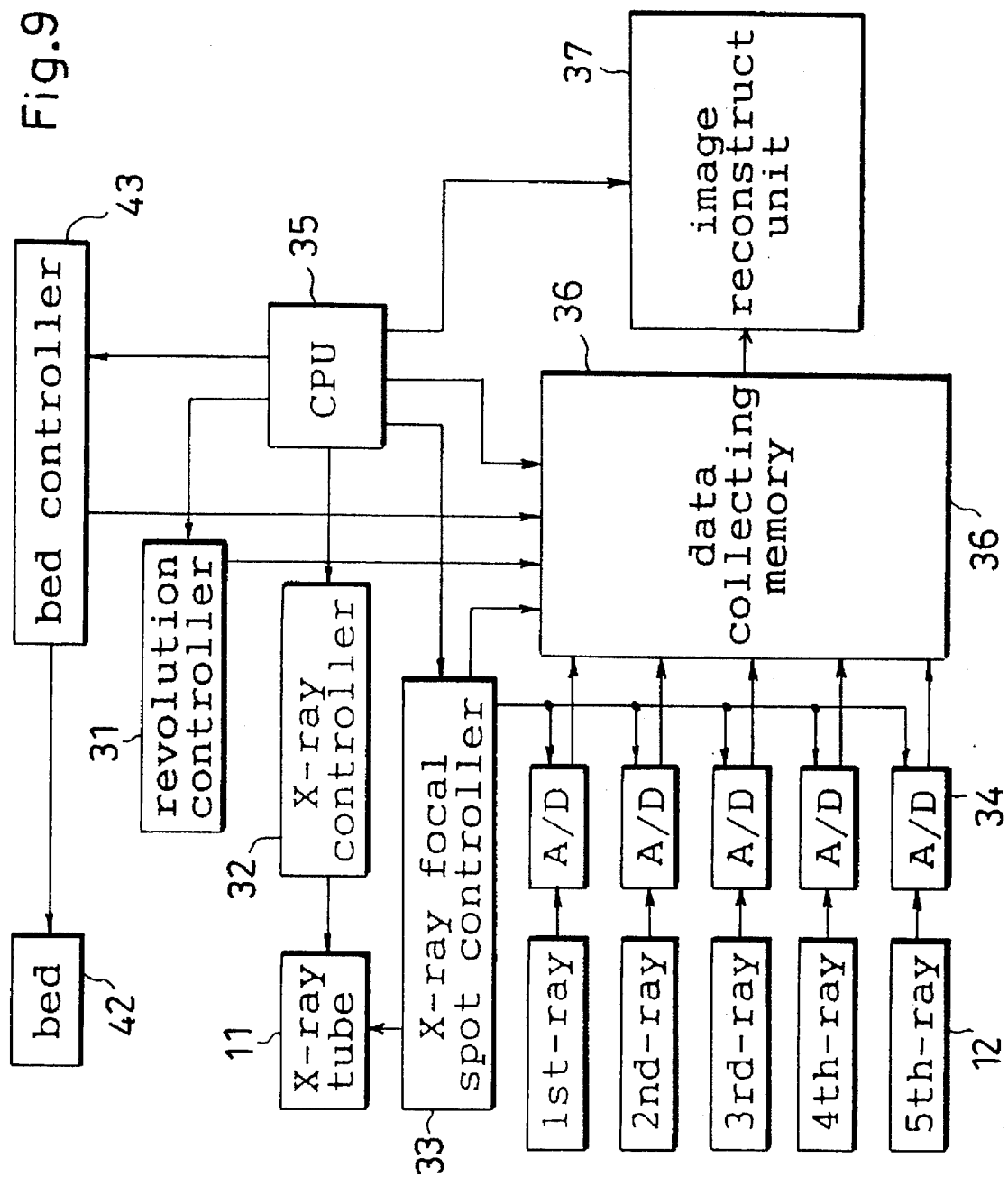

X-RAY CT APPARATUS

This application is a continuation of application Ser. No. 08/429,299 filed Apr. 24, 1995, now abandoned.

BACKGROUND OF THE INVENTION

(1) Field of the Invention

This invention relates to X-ray CT (Computer Tomography) apparatus for use in medical and industrial fields to scan an object with X-ray beams and obtain three-dimensional images of the interior of the object, and particularly to X-ray CT apparatus for carrying out helical scans.

(2) Description of the Related Art

An X-ray CT apparatus irradiates an object under examination with X-ray beams from all directions through 360° in each plane (slice plane) of the object, and acquires projection data for the respective directions through 360° by detecting intensity of transmitted X rays. Then, the apparatus puts the projection data to a reverse projection to reconstruct a distribution of X-ray absorption rates (sectional image) on the slice plane. In order to acquire projection data in the directions through 360° by means of X-ray beams, an X-ray tube usually is revolved round the object to describe a circular path on the slice plane, and the X-ray beams generated by the X-ray tube are directed toward the axis of revolution. The object is placed adjacent the axis of revolution, and an X-ray detector opposed to the X-ray tube across the object detects X-ray beams transmitted through the object. In this way, the above slice plane of the object is scanned by X-ray beams to provide projection data. The X-ray detector may include a plurality of detecting elements arranged in the form of an arc. This X-ray detector is revolved with the X-ray tube while maintaining the mutually opposed relationship across the object. Alternatively, the X-ray detector may include numerous detecting elements fixedly arranged on an entire circumference.

It is desired from the point of view of improved X-ray use efficiency to arrange the detecting elements of the X-ray detector two-dimensionally including a direction perpendicular to the slice plane as well. A specific example of X-ray CT apparatus commercially available today includes detecting elements arranged in two rows to collect data for two slices simultaneously. Further, an X-ray CT apparatus has been manufactured for trial, which employs an X-ray image intensifier as X-ray detector for continuously detecting X-ray incidence positions in the direction of a slice plane as well as the direction perpendicular thereto.

In addition, an X-ray CT apparatus of what is known as the helical scan type has been developed recently. This apparatus moves an object in a direction perpendicular to slice planes thereof while revolving an X-ray tube to scan the object with X-ray beams emitted from circumferential positions. As a result, the X-ray beams scan not only a single slice plane as above, but helically scan a three-dimensional space having a width in the direction perpendicular to the slice plane. The data thereby collected are put to a reverse projection in a helical mode to reconstruct a three-dimensional image of a section of the object.

FIG. 1 shows a helical scan type X-ray CT apparatus employing an X-ray detector having detecting elements in a two-dimensional arrangement. As seen in FIG. 1, a gantry 10 houses a single-focus X-ray tube 17 and an X-ray detector 12, and defines a tunnel (not shown) centrally thereof. The X-ray tube 17 and X-ray detector 12 are supported by a rotary support, not shown, to be revolvable together while maintaining a mutually opposed relationship across the tunnel. In this example, the X-ray detector 12 includes five rows of X-ray detecting elements juxtaposed in the direction perpendicular to a plane defined by a revolving circumference. A patient 41 is placed on a top board of a bed 42, and the top board is movable (sideways in FIG. 1) to introduce the patient 41 into the tunnel of gantry 10.

Assuming that a plane (slice plane) in which the X-ray tube 17 and X-ray detector 12 are revolvable is X–Y plane, and that the direction perpendicular to that plane (along the axis of revolution) is Z direction, this Z direction corresponds to the axial direction of patient 41 in which the patient 41 is introduced. When the patient 41 is moved in Z direction during a revolution of X-ray tube 17 and X-ray detector 12, a helical scan of the patient 14 is effected by X-ray beams emitted from the X-ray tube 17 as shown in FIG. 2. This provides X-ray transmission data relating not only to one slice plane perpendicular to the body axis of patient 41 but to an entire solid having a thickness in the axial direction. The pitch of this helical scan cannot be as large (coarse) as an entire width D (in Z direction) of X-ray detector 12 as shown in FIG. 1, but has to be about the same as width "d" of one detecting element as shown in FIG. 2. A three-dimensional image of the patient 41 in the above scan range may be reconstructed by helically projecting the data obtained in a helical form as above.

In the above conventional construction, as shown in FIG. 1, the X-ray tube 17 generates X-ray beams which diverge in a conical form from one focal spot F0 to enter the X-ray detector 12 (having five rows of detecting elements), thereby providing data. The helical scan having a coarse pitch would provide a large amount of data resulting from incident X-ray beams having data acquiring directions not perpendicular to Z-axis. An image reconstructed from such data is vulnerable to artifacts. Since the helical scan cannot have a large pitch as noted above, a time-consuming scanning operation is required to acquire data for a three-dimensional region having a length in the axial direction.

SUMMARY OF THE INVENTION

This invention has been made having regard to the state of the art noted above, and its object is to provide an X-ray CT apparatus capable of completing a helical scan in a short time by enlarging the helical scan pitch while avoiding artifacts appearing in a reconstructed image.

The above object is fulfilled, according to this invention, by an X-ray CT apparatus for scanning an object with X-ray beams to obtain three-dimensional images of the interior of the object, the apparatus comprising:

an X-ray generator revolvable to describe a circular path on a plane of revolution, and having a plurality of X-ray focal spots (focal positions) arranged in a direction perpendicular to the plane of revolution; an X-ray detector opposed to the X-ray generator, and having a plurality of detecting elements arranged in a direction along a circumferential edge of the plane of revolution and in the direction perpendicular to the plane of revolution;

a revolution controller for revolving the X-ray generator and the X-ray detector without varying a positional relationship therebetween, and outputting angle information;

a moving device for moving the object introduced into a space between the X-ray generator and the X-ray detector, relative to the X-ray generator and the X-ray detector, during a revolution of the X-ray generator, in the direction perpendicular to the plane of revolution, by a distance exceeding a width of at least one of the detecting elements per revolution of the X-ray generator, the moving device outputting moving amount information indicative of the distance;

an X-ray focal position controller for successively switching the plurality of focal positions of the X-ray generator in response to the revolution by the revolution controller, and outputting focal position information; and an image reconstruct unit operable in response to data from the X-ray detector, the angle information from the revolution controller, the moving amount information from the moving device, and the focal position information from the X-ray focal position controller, for reconstructing a three-dimensional image relating to the object by reversely projecting the data in helical form.

The X-ray generator having a plurality of X-ray focal spots (focal positions) and the X-ray detector opposed to the X-ray generator are revolved without varying the mutual positional relationship by the revolution controller. The moving device moves the object relative to the X-ray generator and X-ray detector, during a revolution by the revolution controller. That is, a helical scan is carried out. An amount of relative movement of the object per revolution of the X-ray generator corresponds to a distance exceeding a width, in the direction perpendicular to the plane of revolution, of at least one of the detecting elements (this distance being called a helical scan pitch). At this time, the X-ray focal position controller successively switches the plurality of focal positions of the X-ray generator in response to the revolution by the revolution controller.

Thus, the plurality of focal positions of X-ray generator are switched successively with the revolution of the X-ray generator and X-ray detector by the revolution controller. When a helical scan is carried out at an increased pitch, the X-ray generator at a given rotating angle has positions (focal positions) of the X-ray focal spot in the direction of movement of the object, not jumping from one pitch to another but coinciding with the plurality of X-ray focal positions within the pitch. Thus, despite an increase in the helical scan pitch, no increase occurs with inclination of the direction of X-ray beams detected by the X-ray detector, i.e. inclination of the direction of projection data acquisition. As a result, an image reconstructed from these projection data is free from artifacts.

Preferably, the X-ray detector has the detecting elements arranged opposite, and corresponding in number, to the focal positions of the X-ray generator.

With the detecting elements of the X-ray detector arranged opposite, and corresponding in number, to the focal positions, X-ray beams emitted from the respective focal positions vertically enter the corresponding detecting elements. Thus, an image reconstructed from resulting projection data is free from artifacts.

Preferably, the moving device is operable to move the object by a distance, or by twice the distance, corresponding to a width of the X-ray detector in the direction perpendicular to the plane of revolution, per revolution of the X-ray generator.

No artifacts will appear in a reconstructed image even when the object is moved relative to the X-ray generator and X-ray detector by a distance, or by twice the distance, corresponding to the width of the X-ray detector in the direction perpendicular to the plane of revolution, per revolution of the X-ray generator. Consequently, the moving speed (scan speed) axially of the object is increased to carry out, in a reduced time, a helical scan of an entire three-dimensional region having an increased thickness in the axial direction of the object.

Preferably, the X-ray generator is an X-ray tube including a rotary anode cylinder rotatable about an axis extending perpendicular to said plane of revolution, an electron beam collision device for causing electron beams to collide with the rotary anode cylinder, thereby to generate X-ray beams, and a deflector for deflecting the electron beams axially of the rotary anode cylinder.

An X-ray tube with a rotary anode cylinder may be employed as the X-ray generator having a plurality of X-ray focal positions. Such X-ray generator may be realized extremely easily in practice by the construction to electrostatically or electromagnetically deflect electron beams for collision with the rotary anode cylinder.

Preferably, the deflector includes two magnetic field deflector coils for generating magnetic fluxes in opposite directions, the magnetic field deflector coils being arranged in series between the electron beam collision device and the rotary anode cylinder so that the magnetic fluxes are perpendicular to an axis of the rotary anode cylinder, directions of the magnetic fluxes of the magnetic field deflector coils being switchable to deflect the electron beams emitted at right angles to the rotary anode cylinder.

The electron beams emitted from the electron beam collision device travel along a path bent to a predetermined curvature by the first one of the two magnetic field deflector coils arranged in series between the electron beam collision device and rotary anode cylinder, and then bent by the second coil in the direction opposite to the first bending direction. As a result, the electron beams are directed at right angles to the rotary anode cylinder. The electron beams emitted from this X-ray tube constantly have a substantially circular sectional shape regardless of the focal positions. Thus, this X-ray tube effectively avoids a deterioration in quality of reconstructed images due to an elliptic sectional shape or the like of the electron beams.

Further, the X-ray generator may comprise an X-ray tube including a rotary anode cylinder, two electron beam collision devices for causing electron beams of different accelerating voltages to collide with different positions of the rotary anode cylinder, thereby to generate X-ray beams, and two deflectors for deflecting the electron beams axially of the rotary anode cylinder, the electron beams as deflected being emitted alternately.

With the two electron beam collision devices for alternately emitting two deflected electron beams, the focal positions of one electron beam are successively switched, and during a period of reversing directions to return this electron beam to the first focal position, the focal positions of the other electron beam may be switched successively for emission. Thus, data may be collected efficiently within a short time. Furthermore, since the two deflected electron beams have different energy levels (i.e. high and low energy levels), different X-ray CT images are obtained, thus facilitating acquisition of clinically useful images.

Preferably, each of the two deflectors includes two magnetic field deflector coils for generating magnetic fluxes in opposite directions, the magnetic field deflector coils being arranged in series between the electron beam collision device and the rotary anode cylinder so that the magnetic fluxes are perpendicular to an axis of the rotary anode cylinder, directions of the magnetic fluxes of the magnetic field deflector coils being switchable to deflect the electron beams emitted at right angles to the rotary anode cylinder.

The apparatus according to this invention may further comprise a movable collimator movable in response to switching of the focal positions by the X-ray focal position controller, to limit an emission range of only X rays from a selected one of the focal positions to a width of the X-ray detector in the direction perpendicular to the plane of revolution.

An irradiation exceeding the width of the X-ray detector not only is meaningless, but exposes the object or patient to excessive X rays, i.e. superfluous X-ray beams (not detected by the X-ray detector) or unwanted primary X rays. The movable collimator is effective to protect the object from excessive X-ray irradiation by reducing the ratio of unwanted primary X rays.

Preferably, the movable collimator includes a disk device having a plurality of slits defined peripherally thereof, a drive unit for rotating the disk device at a predetermined speed, and a sensor for detecting a rotating state of the disk device, the X-ray focal position controller being operable in response to the rotating state to switch the focal positions.

The movement of the movable collimator must be synchronized with the switching of the focal positions. Thus, the disk device defining slits is rotated by the drive unit, and the rotation is detected by the sensor. In response to the rotating state detected, the X-ray focal position controller switches the focal positions of the X-ray generator. The movable collimator may have a simple construction since the slits are movable only by rotating the disk device with the drive unit.

Preferably, the disk device includes two disks arranged one above the other to partly overlap each other, with the slits of the disks overlapping each other in each of the focal positions.

Where only one disk is provided, symmetry may be impaired by the slits becoming slanted relative to the detecting elements of the X-ray detector with rotation of the disk. That is, collimating efficiency becomes the lower from the middle focal position toward the focal positions at opposite ends. The two disks placed one above the other diminish the difference in slit configuration between the middle focal position and peripheral focal positions. This realizes an improved symmetry of collimation.

BRIEF DESCRIPTION OF THE DRAWINGS

For the purpose of illustrating the invention, there are shown in the drawings several forms which are presently preferred, it being understood, however, that the invention is not limited to the precise arrangements and instrumentalities shown.

FIG. 9 is a block diagram showing a control and data collecting/processing system according to this invention;

DETAILED DESCRIPTION OF THE PREFERRED EMBODIMENTS

A preferred embodiment of this invention will be described in detail hereinafter with reference to the drawings.

Figure 3:
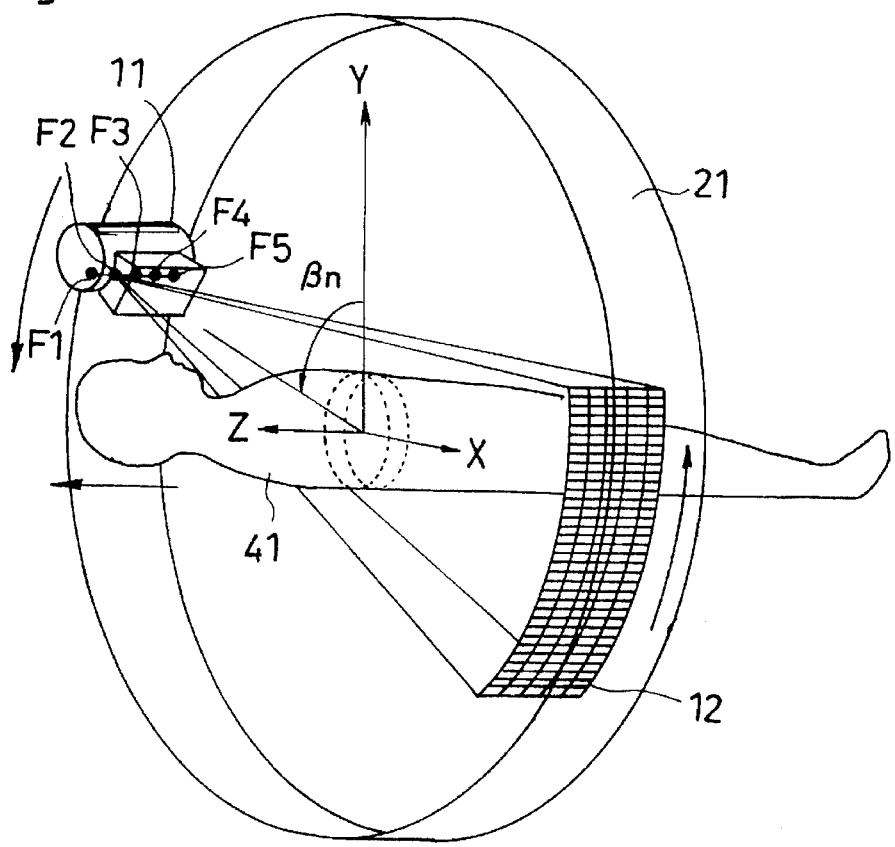
FIG. 3 is a schematic perspective view of an X-ray CT apparatus embodying this invention.

As shown in FIG. 3, an X-ray tube 11 and an X-ray detector 12 are opposited to each other, which are revolvable together (a revolving mechanism being omitted from the drawings) while maintaining this positional relationship. It is assumed here that a plane defined by a cicumference of revolution is an X–Y plane, and that the direction perpendicular thereto is Z direction. A patient 41 is introduced along Z direction into a space between the X-ray tube 11 and X-ray detector 12.

The X-ray tube 11 has a focal spot of X-rays movable in Z direction among positions F1–F5 within a predetermined width D in Z direction. (The construction of this X-ray tube 11 will be described in detail later with reference to FIGS. 13 et seq.) With the X-ray tube 11 revolvable as noted above, the X-ray focal spot is movable along an annular ribbon 21 (which is an imaginary ribbon).

Figure 4:
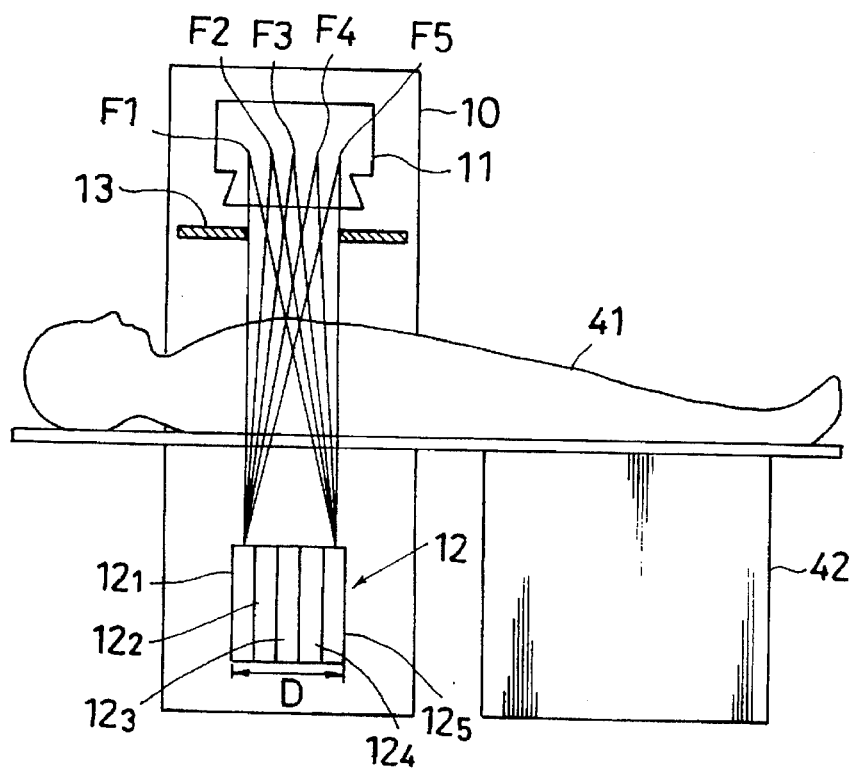
FIG. 4 is a schematic sectional view of the X-ray CT apparatus embodying this invention.

The X-ray detector 12 includes a detection surface in the form of an arc within the X–Y plane and having an effective sensitivity range corresponding to width D in Z direction (see FIG. 4). A plurality of detecting elements are arranged (512 elements in each row) on the curved detection surface. In this embodiment, each detecting element has an effective sensitivity range "d" in Z direction, and such detecting elements are arranged in five rows $12_1$–$12_5$ (d=D/5). Thus, five rows of projection data (for five slices) may be collected simultaneously, with each row providing 512 sampling points.

The detecting elements are arranged in five rows $12_1$–$12_5$ corresponding in number and opposed to the positions F1–F5 of the focal spot of X-ray tube 11. With this arrangement, X-ray beams emitted from the respective focal positions F1–F5 enter the corresponding detecting elements at right angles thereto. Consequently, an image reconstructed from the resulting projection data is free from artifacts.

As shown in FIG. 4, the X-ray tube 11 and X-ray detector 12 are mounted in a gantry 10 defining a tunnel (not shown) centrally thereof. The X-ray tube 11 and X-ray detector 12 are supported by a rotary device not shown, to be revolvable together while maintaining the opposed relationship across the tunnel. The gantry 10 further includes a collimator 13 for collimating the X-ray beams in the axial direction of patient 41 (i.e. in the direction of slice thickness). The patient 41 is placed on a top board of a bed 42, the top board is movable in Z direction to move the patient 41 in Z direction relative to the tunnel of gantry 10.

Figure 1:
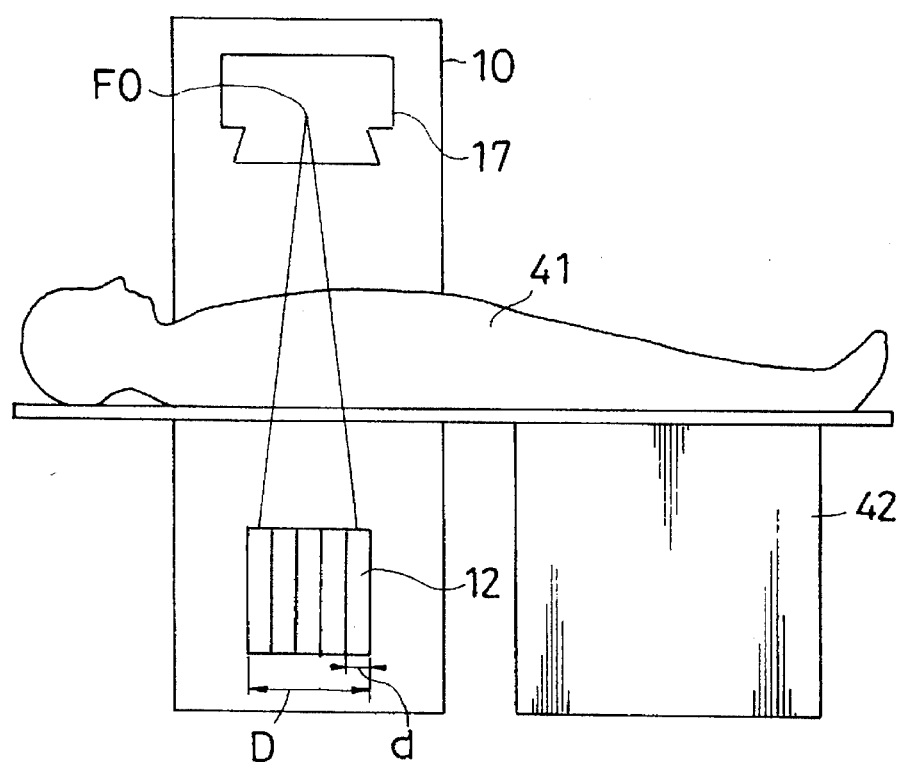
FIG. 1 is a schematic sectional view of an X-ray CT apparatus known in the art.
Figure 2:
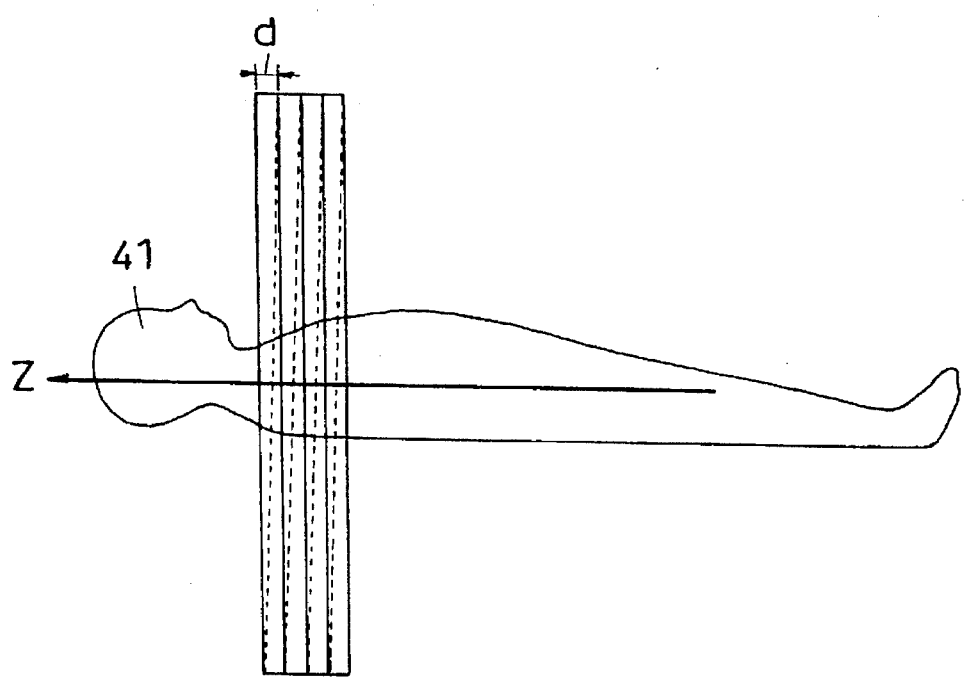
FIG. 2 is a schematic side view showing a helical scan known in the art.
Figure 5:
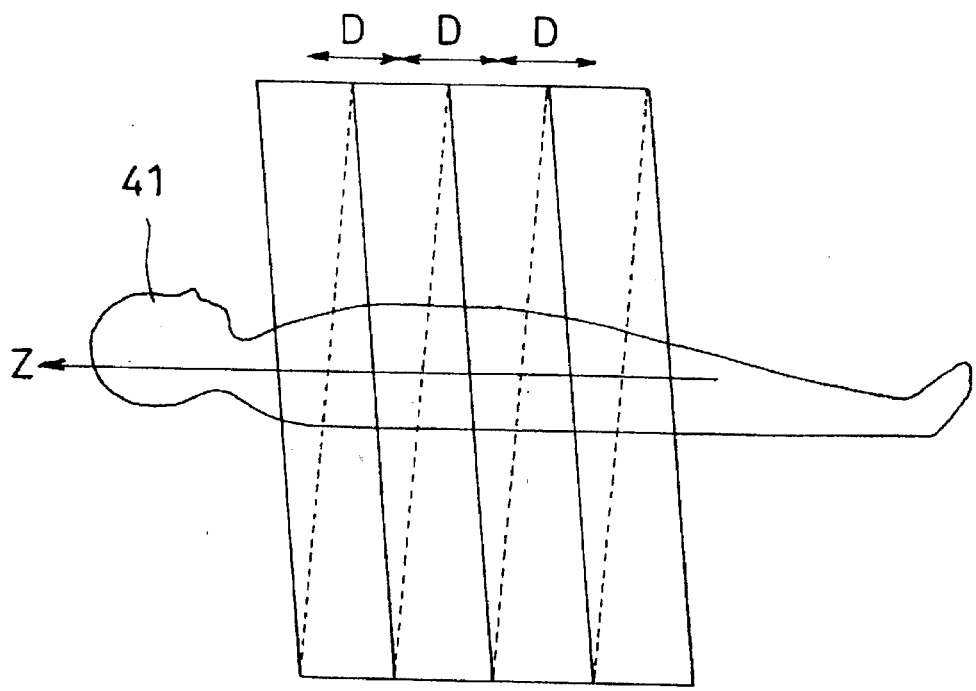
FIG. 5 is a schematic side view showing a helical scan according to this invention.
Figure 6A:
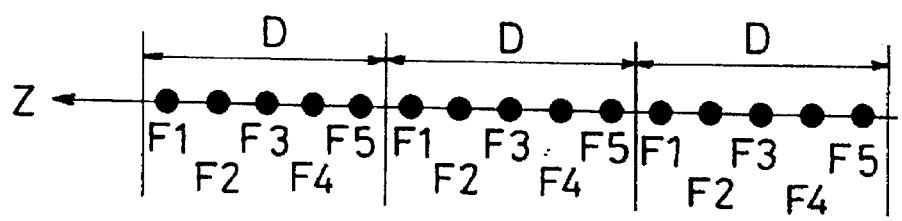
FIGS. 6A and 6B are schematic views showing focal positions in Z direction.
Figure 6B:
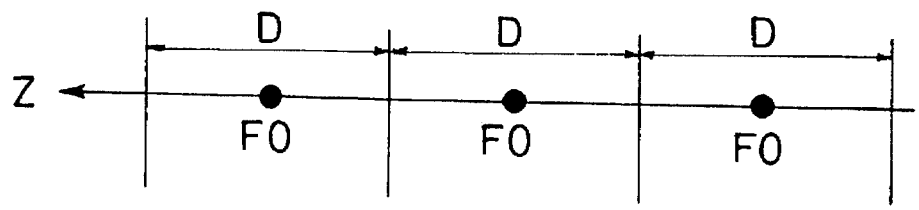

The patient 41 is moved in an amount corresponding to width D for each revolution of X-ray tube 11 and X-ray detector 12, to effect a helical scan of pitch D as shown in FIG. 5. Assuming that the X-ray tube 11 is at a given revolving angle βn, the X-ray tube 11 per se is displaced by distance D in Z direction with each helical scan as shown in FIG. 6A. However, since the focal spot of X rays is movable at high speed among focal positions F1–F5 inside the X-ray tube 11, the focal spot has intervals "d" (=D/5) in Z direction despite the helical scan at pitch D. Thus, the helical scan is made at pitch "d" as far as the focal spot of X rays is concerned. With the conventional X-ray tube 17 having a fixed focal position as shown in FIG. 1, the positions of focal spot F0 in Z direction correspond to intervals at pitch D as shown in FIG. 6B.

Figure 7A:
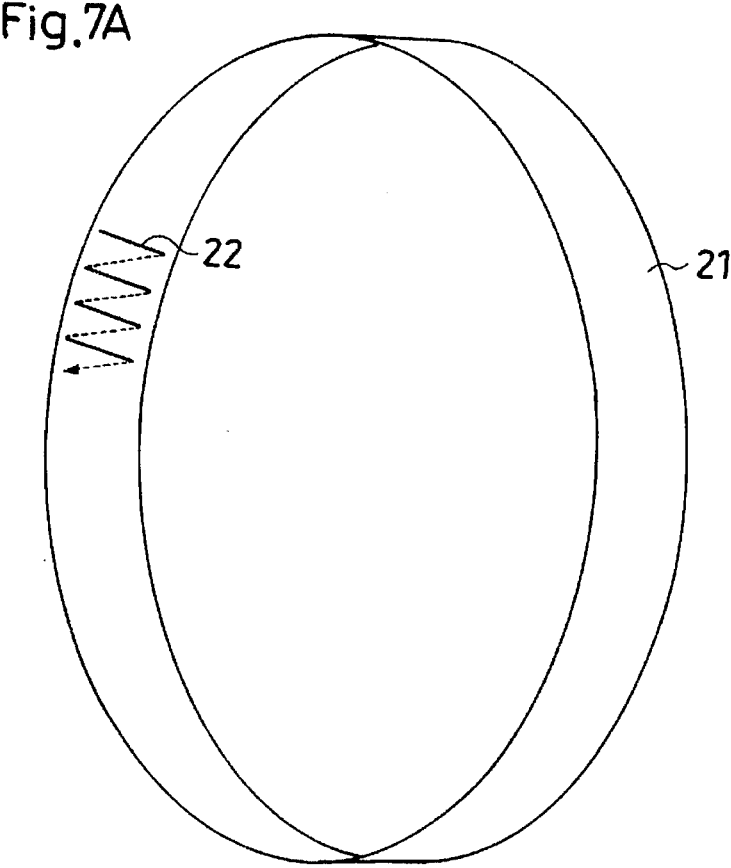
FIGS. 7A and 7B are schematic views each showing a locus of movement of an X-ray focal spot.
Figure 7B:
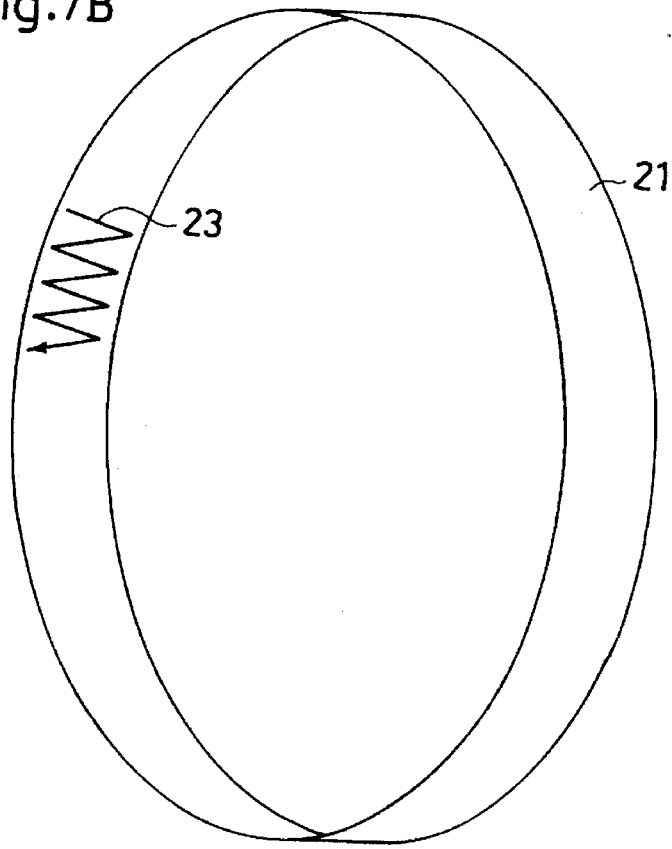
Figure 8:
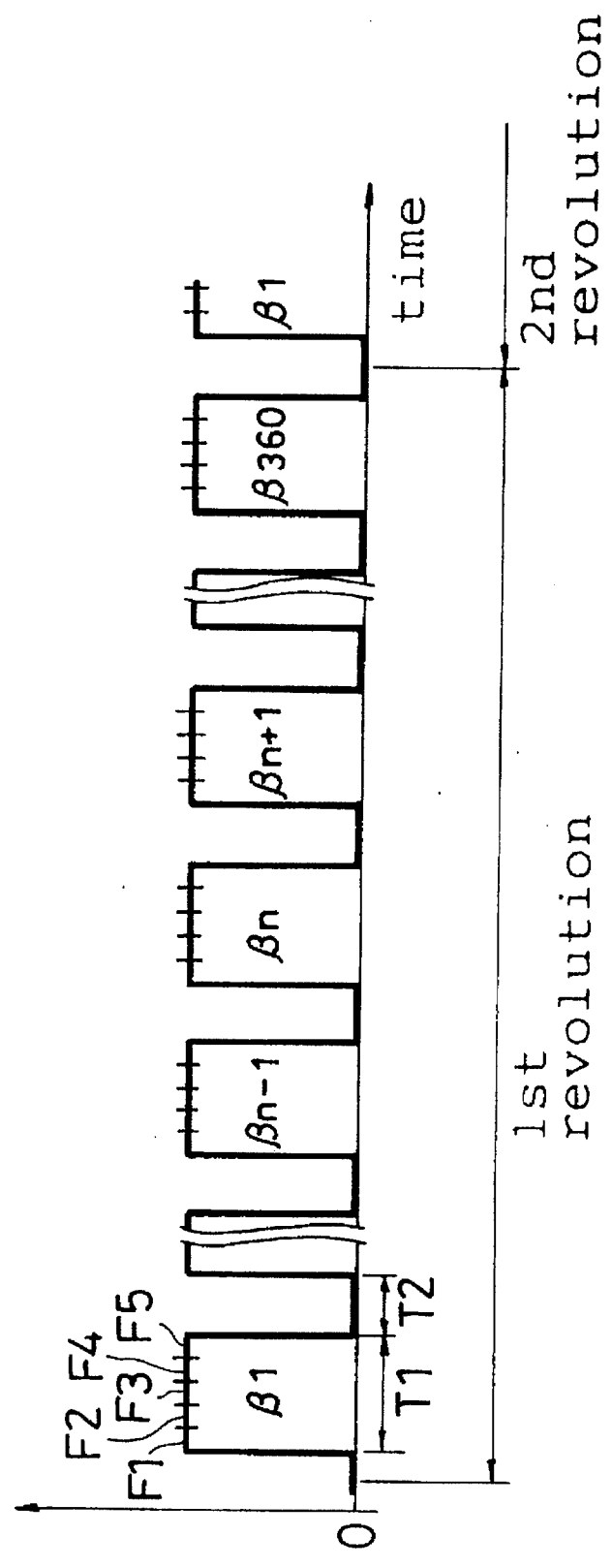
FIG. 8 is a time chart showing variations in the amount of X rays generated.

The X-ray tube 11 is movable on a circular path, with the focal spot (focal position) of X rays reciprocating at high speed. Consequently, the focal spot of X rays moves on a plane of ribbon 21 as shown in FIGS. 3, 7A and 7B (a locus of movement being denoted by 22 and 23). In FIG. 7A, X rays are generated only when the focal spot moves in one direction (i.e. during forward movements as shown in solid lines), and suspended when the focal spot moves in the opposite direction (i.e. during backward movements as shown in dotted lines). In FIG. 7B, X rays are generated during the forward and backward movements. Thus, X rays are used effectively.

Where X rays are turned on and off as shown in FIG. 7A, the quantities of X rays generated are as shown in FIG. 8. In FIG. 8, βn represents a view (a rotating angle of X-ray tube 11 as shown in FIG. 3). In this embodiment, 360 projection data are obtained each covering a view at each angle 1°. That is, in one revolution of X-ray tube 11, X rays are emitted during 360 periods of time T1 corresponding to views <1 to β360, respectively, and suspended during intervening periods of time T2. The focal spot of X rays moves in one direction (i.e. forward) during the periods T1, and in the opposite direction (i.e. backward) during the periods T2. Each period T1 is dividable into five units of time corresponding to focal positions F1, F2, F3, F4 and F5, respectively.

Referring to FIG. 9, the X-ray tube 11 is operable to turn X rays on and off under control of an X-ray controller 32. The focal positions F1–F5 in the X-ray tube 11 are controlled by an focal spot controller 33. The rotary device for revolving the X-ray tube 11 and X-ray detector 12 in the gantry 10 is controlled by a revolution controller 31. Controls for moving the top board of bed 42 are effected by a bed controller 43. The bed controller 43, revolution controller 31, X-ray controller 32 and focal spot controller 33 are all controlled in a coordinated way by a CPU 35.

For example, X rays are emitted as shown in FIG. 8 during one period T1 when the X-ray tube 11 is at the rotating angle of 1° for collecting data of view β1. During this period T1, the focal spot controller 33 causes the focal spot of X rays to move at high speed from position F1 to position F5. The focal spot controller 33 transmits to analog-to-diginal (A/D) converters 34 focal position information indicating positions of the focal spot of X rays (which may be in the form of signals indicating timing for dividing period T1 into five equal units). The A/D converters 34 are provided for the respective rows in the X-ray detector 12. In this embodiment, the X-ray detector 12 includes five rows $12_1$–$12_5$ juxtaposed in Z direction as shown in FIG. 4, and hence five A/D converters 34 are provided. When the focal spot of X rays is moving to position F1, the five A/D converters 34 are operated to carry out sampling and A/D conversion simultaneously, to obtain 5×512 data from the first to fifth rows. These data are stored in a data collecting memory 36 along with the focal position information (indiating F1) from the focal spot controller 33, angle information (indicating β1) from the revolution controller 31, and movement information (indicating a position in Z direction of patient 41) from the bed controller 43. The 5×512 data collected for view β1 and focal position F1 are referred to hereinafter as data (β1, F1).

A data collecting operation similar to the one for focal position F1 is repeated for focal positions F2–F5. The data collecting operations for focal positions F1–F5 are repeated for 360 views β1 to β360 in one revolution, to acquire 5×512 two-dimensional data corresponding to (βn, Fi) ("n" being 0 to 360, and "i" being 1 to 5). The revolution for collecting these data is repeated M times (with the patient 41 moved by distance D per revolution).

Figure 10A:
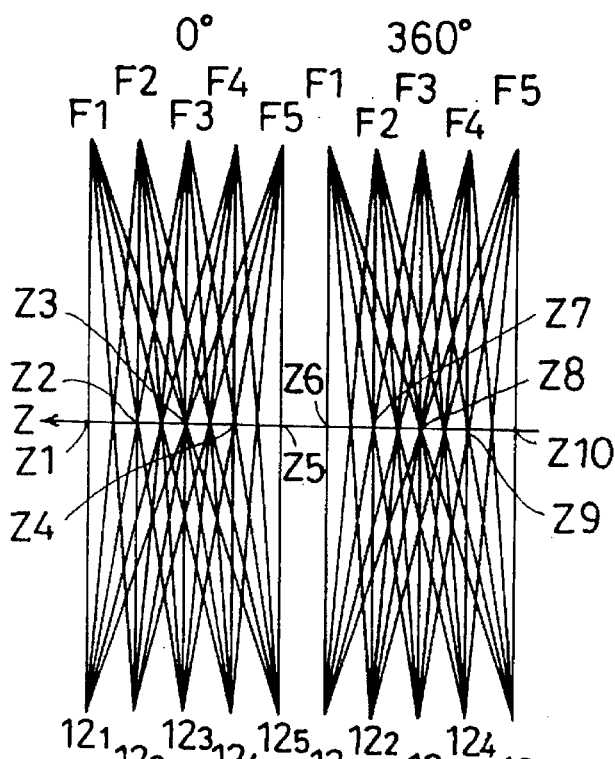
FIGS. 10A and 10B are schematic views showing states of X-ray beams according to this invention.

When the X-ray tube 11 is at angle 0, as shown at the left side of FIG. 10A, X-ray beams are emitted from each of the five focal positions F1–F5, and enter each of the detecting elements in five rows $12_1$–$12_5$ (the X rays travel from top to bottom in the drawing), to acquire a total of 25 projection data. With regard to each of positions Z1–Z5 in Z direction adjacent the body axis of patient 41, data are acquired from X-ray beams passing at right angles through positions Z1–Z5.

Figure 10B:
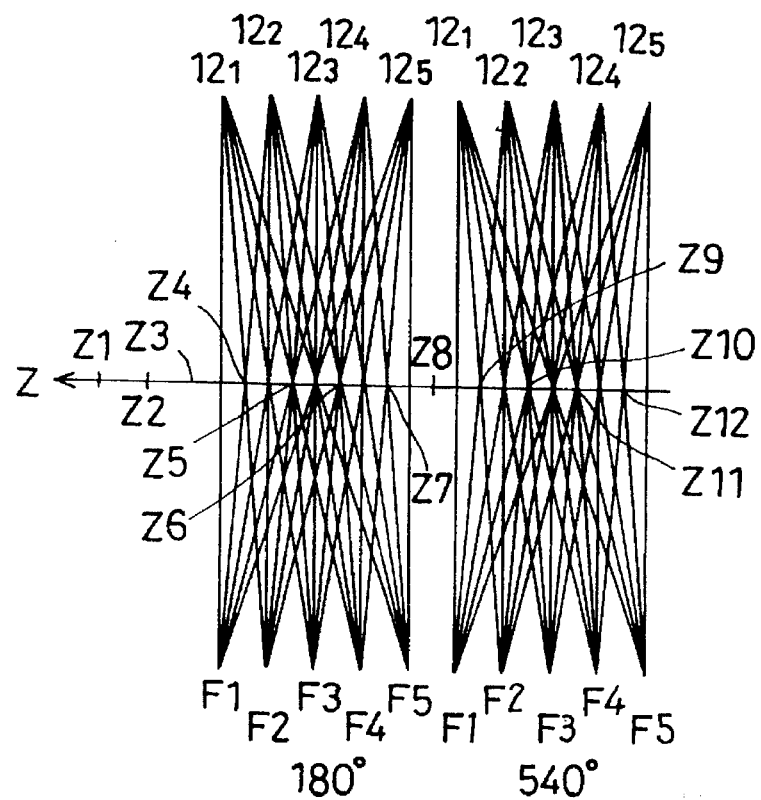

When the X-ray tube 11 is at angle 180°, as shown at the left side of FIG. 10B, X-ray beams are emitted upward from each of the five focal positions F1–F5 located below, and enter each of the detecting elements in five rows $12_1$–$12_5$ located above, to acquire a total of 25 projection data. At this time, the patient 41 has moved by distance D/2 leftward in Z direction, and hence X-ray beams have shifted by distance D/2 rightward with reference to the patient 41.

When the X-ray tube 11 is at angle 360°, X-ray beams travel as shown at the right side of FIG. 10A. When the X-ray tube 11 has revolved further by 180° (540° from the original position) X-ray beams travel as shown at the right side of FIG. 10B. It will be seen from the states of X-ray beams shown in FIGS. 10A and 10B that data are acquired from X-ray beams traveling pependicular to Z direction in positions Z1–Z5 adjacent the body axis of patient 41.

When transmission data of such X-ray beams are stored in the data collecting memory 36, an image reconstruct unit 37 carries out a two-dimensional convolution of the 5×512 two-dimensional data corresponding to each of (βn, Fi), and then a reverse projection of the data to each volumetric lattice point in the original space. That is, the 5×512 data are reversely projected along the passages of the X-ray beams providing the data. This operation is repeated for each of Fi and βn to cover one revolution. The data are reversely projected from each direction through at least 180° for each point in the original space, to reproduce image data for that point. This operation is repeated M times per revolution to reproduce three-dimensional data for a region having a width of D×M in Z direction, excluding width D, i.e. D/2 at each end of the region scanned in the revolutions made M times.

For comparison purposes, the prior art (FIG. 1) will be described, which provides only one fixed focal spot F0 of X rays and helical scan pitch D. It has been noted hereinbefore that, as shown in FIG. 6B, the prior art provides a focal interval D for a given view. When the X-ray tube is at angle 0°, as shown at the left side of FIG. 11A, X rays are emitted downward from the spot F0, and enter each of the detecting elements in five rows to acquire data. When the X-ray tube is at angle 180° as shown at the left side of FIG. 11B, X rays are emitted upward from the spot F0 located below and shifted by D/2 rightward, and enter each of the detecting elements in five rows to acquire data. When the X-ray tube is at angle 360°, data are collected from X-ray beams in the same way as at the left side of FIG. 11A but the X-ray beams are shifted by distance D rightward. When the X-ray tube is at angle 540°, data are collected from X-ray beams in the same way as at the left side of FIG. 11B but the X-ray beams are shifted by distance D rightward therefrom.

Figure 11A:
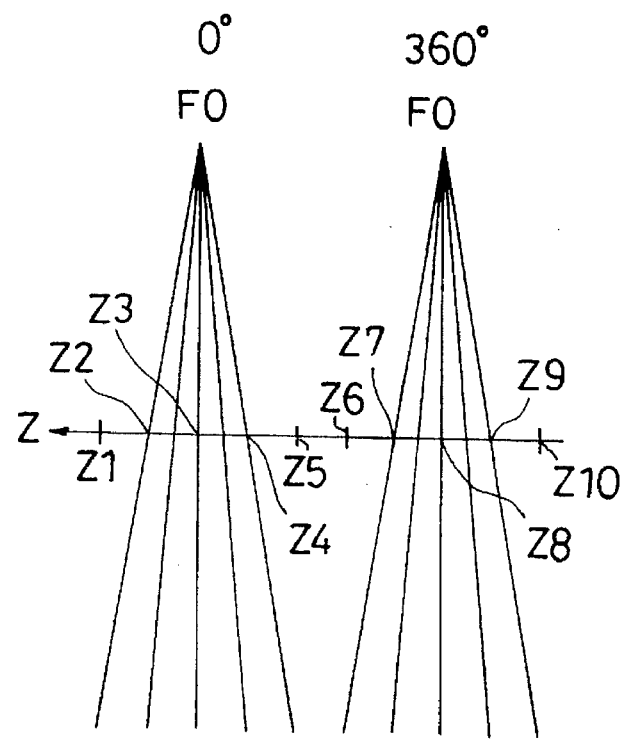
FIGS. 11A and 11B are schematic views showing states of X-ray beams according to the prior art.
Figure 11B:
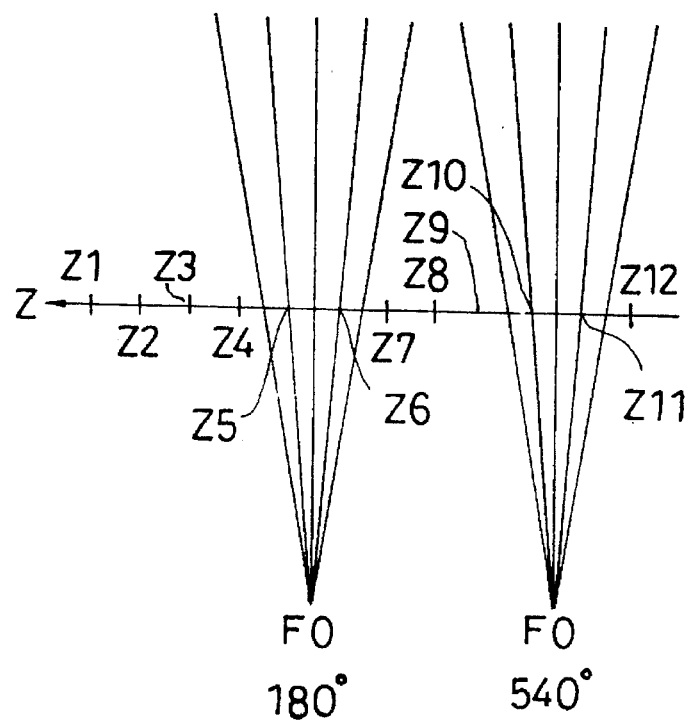

The following facts will be understood from FIGS. 11A and 11B. With regard to a given point between Z5 and Z6 on Z-axis, data are obtained from X-ray beams traveling at right angles to Z-axis when the X-ray tube is at and adjacent 180°. The X-ray beams traveling through this given point are all slanted from the direction perpendicular to Z-axis when the X-ray tube is at other angles. X-ray beams pass through the given point when the X-ray tube is at angles ranging from 90° to 270°. When the X-ray tube is at angle 90°, only the one at the right end of the five X-ray beams emitted from focal spot F0 passes through this given point. When the X-ray tube is at angle 270°, only the X-ray beam at the left end passes through this given point. This applied to all points on Z-axis. Thus, of the projection data within at least 180° for reconstructing each of slice planes Z1–Z12, only one view (i.e. 180° view) coincides with that slice plane (i.e. at right angles to Z-axis) in the strict sense. The projection data for all the other views are not at right angles to Z-axis, and what is worse, they are slanted by considerable degrees from the direction perpendicular thereto. As a result, artifacts will appear in images reconstructed by reversely projecting such projection data within 180°.

On the other hand, where the focal spot of X rays is moved at high speed among focal positions F1–F5, the X-ray tube 11 at any rotating angles causes some X-ray beams to pass at right angles to Z-axis through all of positions Z1–Z12 on Z-axis as noted hereinbefore. Each of the 180 projection data (each of the 180° views) for reconstructing any one of the slice planes Z1–Z12, in the strict sense, always includes data based on an X-ray beam having traveled parallel to that slice plane. Consequently, images of slices Z1–Z12 reconstructed by reversely projecting such projection data are free from artifacts.

Figure 12:
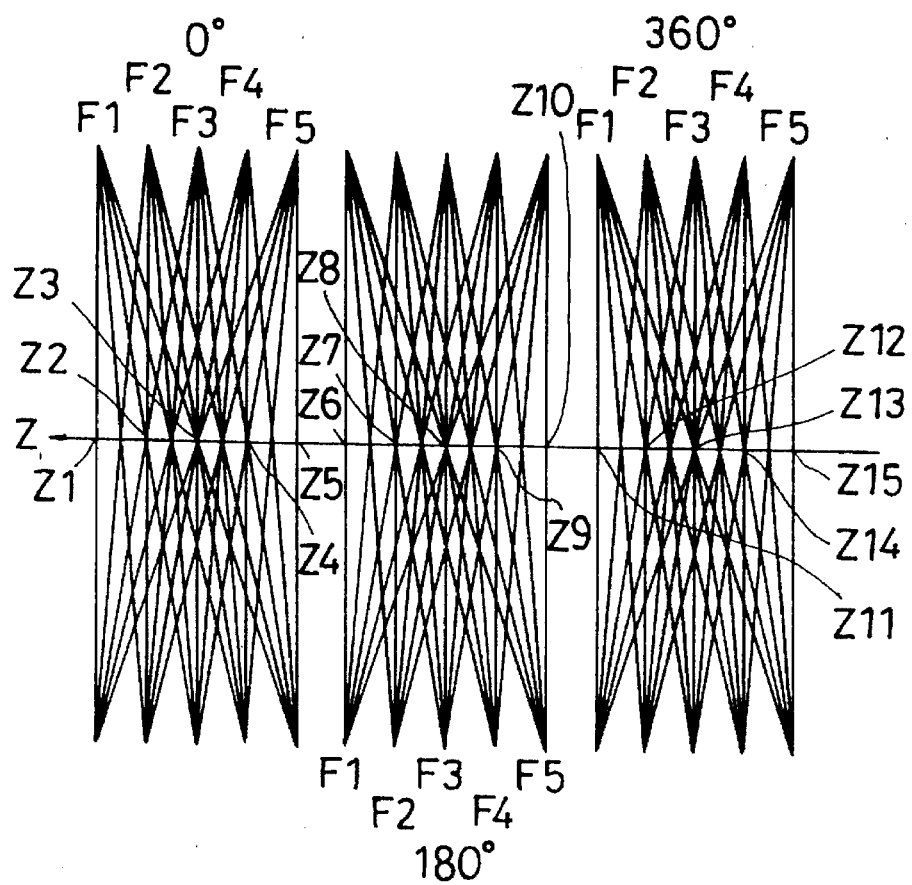
FIG. 12 is a schematic view showing states of X-ray beams in another embodiment of this invention.

FIG. 12 shows a state of X-ray beams where helical scans are made at pitch 2 D, as opposed to pitch D described above. In the example shown in FIG. 12, the X-ray beams emitted from angles 0° and 360° do not overlap those emitted from angle 180° (because of a shift by distance D). Thus, FIG. 12 depicts X-ray beams without dividing them into "A" and "B" as in FIGS. 10A, 10B, 11A and 11B. It will be seen from FIG. 12 that, in the case of helical scan pitch 2 D also, any view for each slice plane always includes projection data based on an X-ray beam having traveled through that slice plane at right angles to Z-axis. Thus, in this case, as in the case of helical scan pitch D, artifacts are eliminated from reconstructed images. In this case, three-dimensional data may be reproduced for a region having a width of D×(2M−1) in Z direction, excluding width 2 D, i.e. D at each end of the region scanned in the revolutions made M times.

Figure 13:
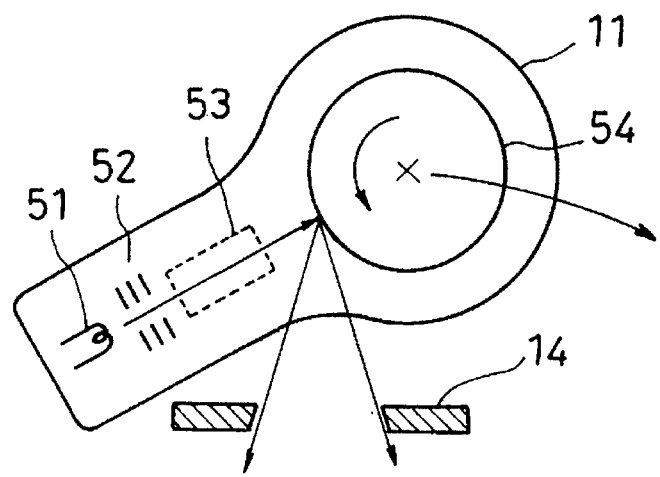
FIG. 13 is a schematic sectional view of an X-ray tube.
Figure 14:
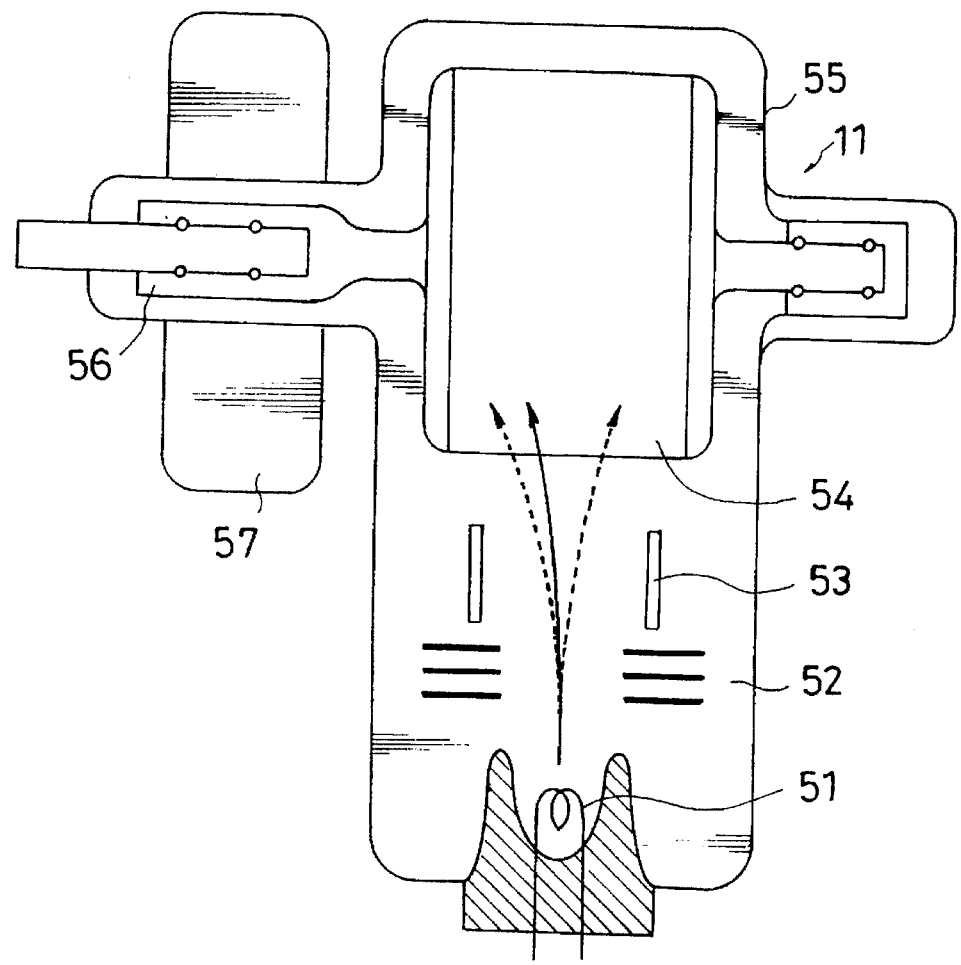
FIG. 14 is a schematic sectional view of the X-ray tube seen from a different direction.

FIGS. 13 and 14 show a construction of X-ray tube 11 capable of moving the focal spot at high speed in the direction of thickness of a slice plane as described above. FIG. 13 is a schematic sectional view of the X-ray tube 11. FIG. 14 is a schematic sectional view of the X-ray tube seen from a different direction. As seen, electron beams generated from a filament 51 pass through accelerating electrodes 52 and an electrostatic deflector electrode plate 53 to collide with a rotary anode cylinder 54. The rotary anode cylinder 54 is rotatable about a center axis thereof extending perpendicular to the plane of revolution of the X-ray tube 11. X-ray beams are generated by the electron beams colliding with the rotary anode cylinder 54, and are emitted toward the patient through the collimator 14 which collimates the X-ray beams in the slice planes.

As shown in FIG. 14, the filament 51, accelerating electrodes 52, electrostatic deflector electrode plate 53 and rotary anode cylinder 54 are arranged in a vacuum enclosure 55. The rotary anode cylinder 54 is rotatably supported through bearings, and is driven through a rotor 56 by a stator 57 disposed outside the enclosure 55. Power is supplied to the rotary anode cylinder 54 through the bearings as in the case of an ordinary umbrella type rotary anode disk. (Power may be supplied by brush electrification or thermionic emission instead of bearing electrification as long as the rotary anode cylinder 54 is rotated at high speed.) The axis of rotation of the rotary anode cylinder 54 extends parallel to the axis of revolution (Z-axis) of X-ray tube 11 and X-ray detector 12, so that no excessive load acts on the rotation sustaining mechanism (bearings) of rotary anode cylinder 54.

Electrostatic fields are variable with the strength and polarity of a potential applied to the electrostatic deflector electrode plate 53, to vary the degree of deflection of the electron beams passing therethrough. Thus, by varying the strength and polarity of the potential applied to the electrostatic deflector electrode plate 53 for acceleration, positions of the electron beams colliding with the rotary anode cylinder 54 are moved along the center axis of the cylinder 54 as shown in FIG. 14, to move the focal spot of X rays at high speed in the direction of slice thickness.

Figure 15:
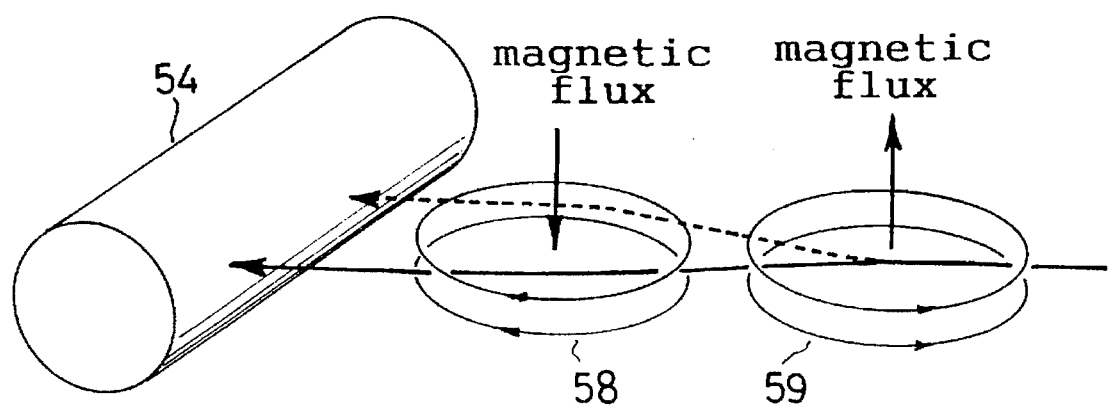
FIG. 15 is a schematic perspective view of a modified deflecting device.

Magnetic fields may be used in place of the electric fields for deflecting the electron beams along the center axis of the rotary anode cylinder 54. As shown in FIG. 15, for example, magnetic field deflector coils 58 and 59 may be used. These magnetic field deflector coils 58 and 59 are arranged in series between the filament 51 and rotary anode cylinder 54, with magnetic fluxes directed perpendicular to the center axis of rotary anode cylinder 54. By causing currents to flow in the directions shown in FIG. 15, generating the magnetic fluxes in the directions shown (in opposite directions), the electron beams are deflected as shown in a solid line. By reversing the directions of the currents, the magnetic fluxes are also reversed to deflect the path of electron beams as shown in a dotted line. Specifically, the first coil 59 bends the path by a predetermined curvature, and then the second coil 58 bends the path in the direction opposite to the bending direction of the first coil 59. Thus, the electron beams may be deflected by the magnetic fields formed by the two magnetic defector coils, to realize the advantage of the electron beams colliding with the rotary anode cylinder 54 always at right angles thereto. This causes the electron beams to have constantly a circular sectional shape regardless of the focal positions, thereby to avoid a deterioration in quality of reconstructed images due to an elliptic sectional shape or the like of the electron beams resulting from certain focal positions.

Figure 16:
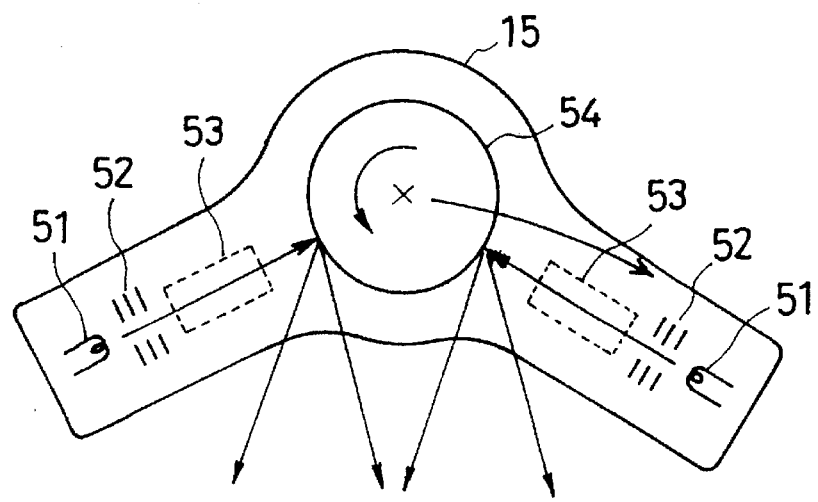
FIG. 16 is a schematic sectional view of a modified X-ray tube.

FIG. 16 shows a bifocal X-ray tube 15 having two of the electron beam generating device shown in FIG. 13 (each having a filament 51, an accelerating electrode 52 and an electrostatic deflector electrode plate 53), for one rotary anode cylinder 54. This X-ray tube 15 can generate X rays from two focal spots simultaneously. However, X-ray beams are generated alternately since a simultaneous generation would make it impossible to distinguish data based on X-ray beams generated from the two different focal spots.

Figure 17:
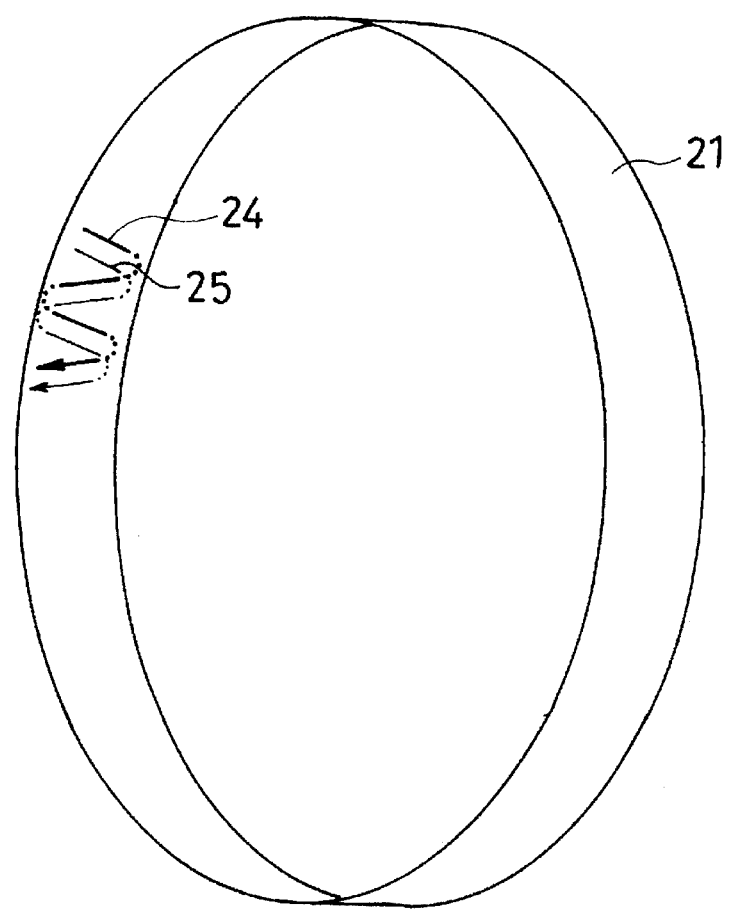
FIG. 17 is a schematic views showing loci of movement of X-ray focal spots occurring with use of the X-ray tube shown in FIG. 16.

Assume that, as shown in FIG. 17, for example, the two focal spots are moved to describe loci 24 and 25, respectively. X rays are emitted from one of the focal spots when this focal spot is moved in one linear direction and opposite direction along solid-line portions of the locus of movement 24. X rays are turned off during periods for reversing directions (to return the X-ray beams to the first focal position after successively switching the focal positions) as shown in dotted-line portions. This is the case with the other focal spot; X rays are emitted when the focal spot is moved in one linear direction and opposite direction along solid-line portions of the locus of movement 25, and turned off during periods for reversing directions as shown in dotted-line portions. While one of the focal spots is reversing directions, the other focal spot moves linearly, whereby data are collected alternately from two rotating angles and efficiently within a short time. Further, different voltages may be applied to the accelerating electrodes 52 to generate X rays of different energy levels from the two focal spots. This will provide clinically useful X-ray CT images of two energy levels.

Figure 18:
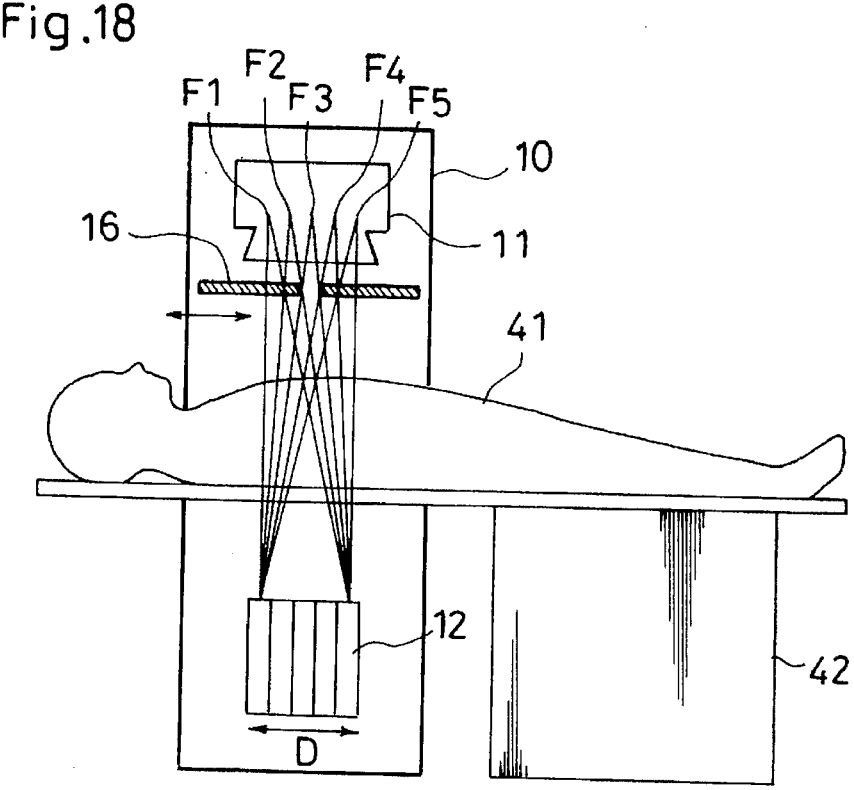
FIG. 18 is a schematic view of a further embodiment of this invention using a movable collimator.

The use of such a bifocal X-ray tube 15 provides a further advantage that a stereo penetration type transmission image may be acquired with ease. That is, the X-ray tube 15 and X-ray detector 12 are stopped at a fixed revolving angle, and only the patient 41 is moved in Z direction with the X-ray tube 15 and X-ray detector 41 standing still. The data thereby collected may be arranged in the direction of movement to provide a [stereo penetration type] transmission image as seen from two focal positions.

Where the focal spot of X rays in the X-ray tube 11 is moved at high speed in the direction of thickness of a slice plane, the collimator 13 for limiting the emission range of X rays to width D in the direction perpendicular to the plane of revolution of X-ray detector 12 should preferably be movable in response to the movement of the focal spot rather than being fixed as described above. FIG. 18 shows a different embodiment employing a movable collimator 16. This movable collimator 16 defines an opening having such a width in the direction of slice thickness that X rays emitted from one focal position diverge to width D in the direction of slice thickness of the effective sensitivity range of X-ray detector 12 (FIG. 18 showing a state where the focal spot is in position F3). This opening is reciprocable as indicated by arrows, in response to the movement of the focal spot. With the X rays generated being limited to the effective sensitivity range D of X-ray detector 12, superfluous primary X rays not entering the X-ray detector 12 are reduced to mitigate the problem of X-ray exposure of patient 41. Where the fixed collimator 13 is used as shown in FIG. 4, the opening must have a large width. In the case of the same focal position F3, for example, X rays will diverge to an extent significantly larger than width D of the effective sensitivity range. This results in a very high ratio of unwanted primary X rays being released without entering the X-ray detector 12.

Figure 19:
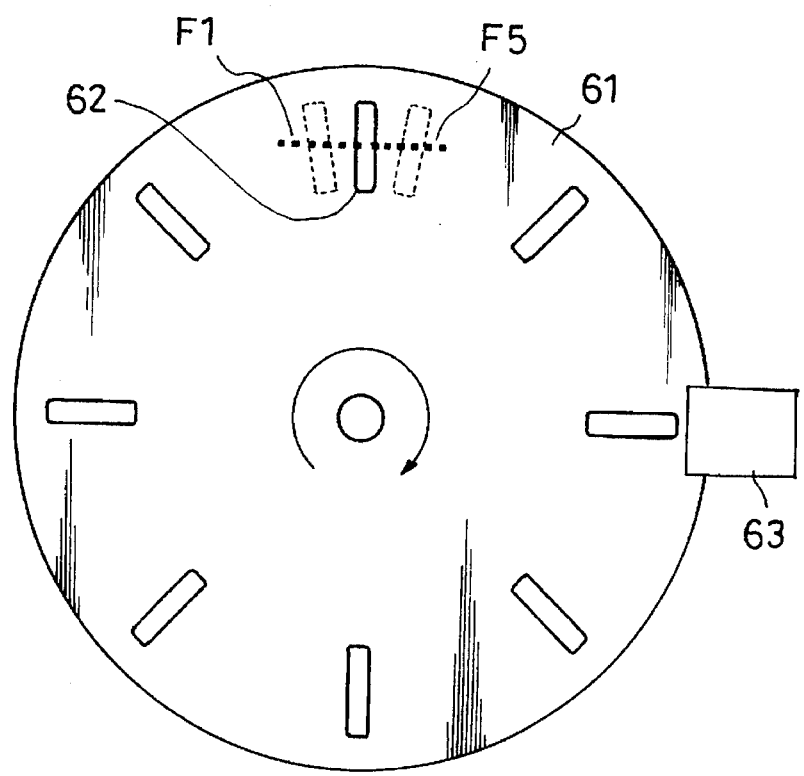
FIG. 19 is a schematic plan view of the movable collimator.

The movable collimator 16 may be modified as shown in FIG. 19, for example. This collimator 16 is in the form of a rotatable disk (circular radiation shielding plate) 61 disposed in front of the X-ray tube 11 (or 15) and defining several slits (radiation transmitting bores) 62. The slits 62 are sized in the order of 20 mm×100 mm, for example. The disk 61 is disposed and rotated as indicated by an arrow such that the slits 62 revolve with the movement of the focal spot of X rays from position F1 to position F5. Since this revolution and the movement of the focal spot of X rays must be synchronized, a photosensor 63 (or a shaft encoder or the like) is provided to detect a motor-driven, high-speed rotation of disk 61. The photosensor 63 transmits a detection signal to the focal spot controller 33 (FIG. 9) to synchronize the movement of the focal spot with the rotation.

Figure 20:
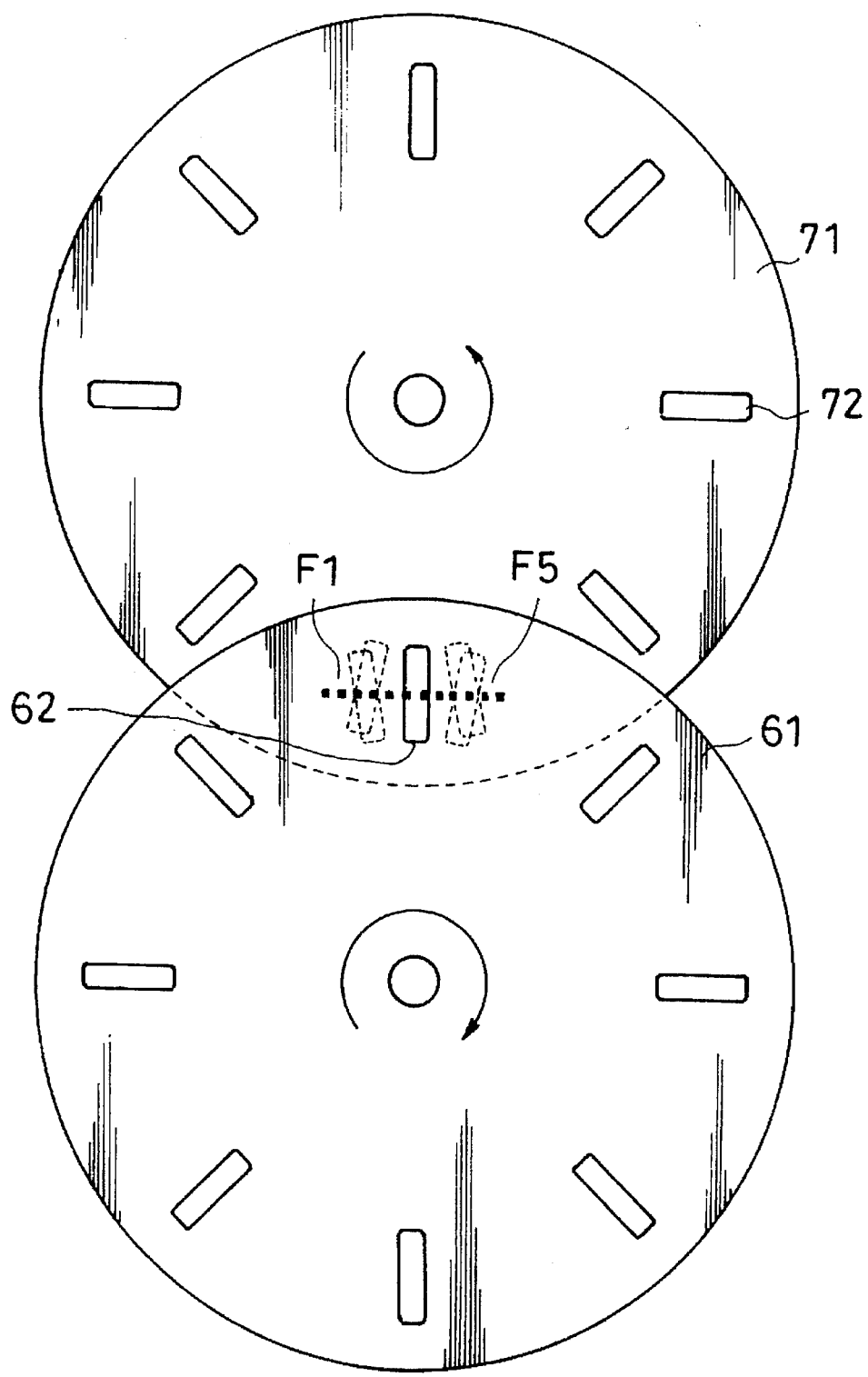
FIG. 20 is a schematic plan view of a modified movable collimator.

As shown in FIG. 20, a disk 71 similar to the disk 61 may be used additionally, such that the two disks 61 and 71 are arranged to partly overlap each other in focal positions F1–F5 of X rays, and rotated in synchronism. With this construction, X rays are collimated by superimposition of slits 62 and 72 in the overlapping portions of the two disks 61 and 71. Thus, the symmetry of collimation is improved upon that provided by the movable collimator shown in FIG. 19.

The present invention may be embodied in other specific forms without departing from the spirit or essential attributes thereof and, accordingly, reference should be made to the appended claims, rather than to the foregoing specification, as indicating the scope of the invention.

What is claimed is:

1. An X-ray CT apparatus for scanning an object with X-ray beams to obtain three-dimensional images of the interior of the object, said apparatus comprising:

X-ray generating means revolvable to describe a circular path on a plane of revolution, and including means for generating a plurality of X-ray focal spots at a plurality of positions arranged in a direction perpendicular to said plane of revolution;

X-ray detecting means opposed to said X-ray generating means, and having a plurality of detecting elements arranged in a direction along a circumferential edge of said plane of revolution and in a plurality of rows perpendicular to said plane of revolution, opposite to, and corresponding in number, to the number of said focal positions of said X-ray generating means;

revolution control means for revolving said X-ray generating means and said X-ray detecting means through plural revolutions in a plurality of angular increments without varying a positional relationship therebetween, and outputting angle information at each angular increment;

moving means for moving said object introduced into a space between said X-ray generating means and said X-ray detecting means, relative to said X-ray generating means and said X-ray detecting means, during each revolution of said X-ray generating means, in said direction perpendicular to said plane of revolution, by a distance exceeding a width of at least one of said detecting elements per revolution of said X-ray generating means, said moving means outputting moving amount information indicative of said distance;

X-ray focal position control means for successively switching said plurality of focal positions of said X-ray generating means at each angular increment of each revolution of said revolution control means and movement of said object by said moving means, and outputting focal position information for each focal position at each angular increment; and image reconstructing means operable in response to data from said X-ray detecting means, said angle information from said revolution control means, said moving amount information from said moving means, and said focal position information from said X-ray focal position control means, for reconstructing a three-dimensional image relating to said object by reversely projecting said data in helical form wherein the total number of focal positions from which data is collected is equal to the number of focal positions per angular increment times the number of angular increments.

2. An apparatus as defined in claim 1, further comprising a movable collimator movable in response to switching of said focal positions by said X-ray focal position control means, to limit an emission range of only X rays from a selected one of said focal positions to a width of said X-ray detecting means in said direction perpendicular to said plane of revolution.

3. An apparatus as defined in claim 2, wherein said movable collimator includes disk means having a plurality of slits defined peripherally thereof, drive means for rotating said disk means at a predetermined speed, and a sensor for detecting a rotating state of said disk means, said X-ray focal position control means being operable in response to said rotating state to switch said focal positions.

4. An apparatus as defined in claim 3, wherein said disk means includes two disks arranged one above the other to partly overlap each other, with said slits of said disks overlapping each other in each of said focal positions.

5. An apparatus as defined in claim 1, wherein said moving means is operable to move said object by a distance, or by twice said distance, corresponding to a width of said X-ray detecting means in said direction perpendicular to said plane of revolution, per revolution of said X-ray generating means. right angles to said rotary anode cylinder.

6. An apparatus as defined in claim 1, wherein said X-ray generating means is an X-ray tube including a rotary anode cylinder, two electron beam collision means for causing electron beams of different accelerating voltages to collide with different positions of said rotary anode cylinder, thereby to generate X-ray beams, and two deflecting means for deflecting said electron beams axially of said rotary anode cylinder, said electron beams as deflected being emitted alternately.

7. An apparatus as defined in claim 6, wherein each of said two deflecting means includes two magnetic field deflector coils for generating magnetic fluxes in opposite directions, said magnetic field deflector coils being arranged in series between said electron beam collision means and said rotary anode cylinder so that said magnetic fluxes are perpendicular to an axis of said rotary anode cylinder, directions of said magnetic fluxes of said magnetic field deflector coils being switchable to deflect said electron beams emitted at right angles to said rotary anode cylinder.

8. An apparatus as defined in claim 1, wherein said X-ray generating means is an X-ray tube including a rotary anode cylinder rotatable about an axis extending perpendicular to said plane of revolution, electron beam collision means for causing electron beams to collide with said rotary anode cylinder, thereby to generate X-ray beams, and deflecting means for deflecting said electron beams axially of said rotary anode cylinder.

9. An apparatus as defined in claim 8, wherein said deflecting means includes two magnetic field deflector coils for generating magnetic fluxes in opposite directions, said magnetic field deflector coils being arranged in series between said electron beam collision means and said rotary anode cylinder so that said magnetic fluxes are perpendicular to an axis of said rotary anode cylinder, directions of said magnetic fluxes of said magnetic field deflector coils being switchable to deflect said electron beams emitted at right angles to said rotary anode cylinder.

* * * * *